United States Patent [19]

Horowitz

[11] Patent Number: 4,806,482

[45] Date of Patent: Feb. 21, 1989

[54] MICROBIAL DEGRADATION OF HYDROCARBONS

[75] Inventor: Amikam Horowitz, Shaker Heights, Ohio

[73] Assignee: The B.F. Goodrich Company, New York, N.Y.

[21] Appl. No.: 203,188

[22] Filed: Jun. 6, 1988

Related U.S. Application Data

[62] Division of Ser. No. 842,528, Mar. 21, 1986.

[51] Int. Cl.[4] .......................... C02F 3/00; C12N 1/26; C12N 1/30; C12R 1/05
[52] U.S. Cl. .................................. 435/262; 435/320; 435/245; 435/249; 435/250; 435/829
[58] Field of Search ............... 435/320, 248, 249, 250, 435/262, 829

[56] References Cited

PUBLICATIONS

Stucki, G. et al. Experientia vol. 39, pp. 1271-1273 (1983).

Primary Examiner—Thomas G. Wiseman
Assistant Examiner—Joan Ellis
Attorney, Agent, or Firm—Roman Saliwanchik; David R. Saliwanchik

[57] ABSTRACT

The subject invention concerns a novel plasmid and its use in a microbial host to degrade a variety of organic compounds. Some of these compounds, such as ethylene dichloride, are undesirable waste products found in various dump sites. The invention also concerns a novel microbe hosting the novel plasmid. The novel plasmid has been shown to encode the gene(s) responsible for the degradation of the organic compounds. Thus, microbes hosting this plasmid, denoted pEDC, can be used to degrade ethylene dichloride, and other compounds.

7 Claims, 1 Drawing Sheet

MICROBIAL DEGRADATION OF HYDROCARBONS

This is a division of application Ser. No. 842,528, filed Mar. 21, 1986.

DESCRIPTION

Background of the Invention

The use of microbes to degrade a variety of noxious wastes to environmentally-acceptable products is an ongoing project in our society. Numerous successes in cleaning the envrironment by such microbial means has given an impetus to the research. The benefits of such microbial cleansing systems is considered to be great in terms of providing a cleaner, and safer, environment, at an acceptable cost. Illustrations of some recent microbial discoveries in this area are found in issued patents. Some of these patents are as follows:

U.S. Pat. No. 4,477,570 concerns the use of *Pseudomonas cepacia* var. niagarous to decompose aromatic halogen-containing organic wastes.

U.S. Pat. No. 4,483,923 claims *Pseudomonas fluorescens* 3P, which is used to remove non-ionic surface active agents and detergents from wastewater.

U.S. Pat. No. 4,490,471 discloses the use of various Pseudomonads for purification of aqueous solutions by degradation of lower alkanols, lower alkanoates, monosaccharides, disaccharides and a variety of methylammonium compounds.

U.S. Pat. No. 4,492,756 relates to the use of a microbe from the genus Hyphomicrobium to degrade compounds which contain methyl groups in aqueous solutions.

U.S. Pat. No. 4,493,895 results from a divisional application wherein the parent application matured into U.S. Pat. No. 4,477,570, described above.

U.S. Pat. No. 4,508,824 uses *Pseudomonas putida* and Pseudomonas aeruginosa to degrade various hydrocarbons.

U.S. Pat. No. 4,511,657 concerns a microbial culture system using the microbes described in U.S. Pat. No. 4,493,895, listed above.

U.S. Pat. No. 4,521,515 claims a novel Pseudomonas bacterium to degrade hydrocarbons such as may be found in an oil spill.

U.S. Pat. No. 4,535,061 claims a specific strain of *Pseudomonas cepacia* and a mixed culture of Pseudomonas and Arthrobacter which are useful to degrade various polychlorinated biphenyls.

U.S. Pat. No. 4,554,075 concerns the use of the white-rot fungus (*Phanerochaete chrysosporium*) for the degradation of chloro-organics.

Several bacteria have been found to degrade chlorinated hydrocarbons. One organism, identified as *Pseudomonas cepacia* var. niagarous, is disclosed in U.S. Pat. No. 4,477,570, referred to above. This organism was reported to degrade a variety of chlorinated toluenes and benzoic acids.

T. Leisinger and his co-workers were the first to describe aerobic biodegradation of ethylene dichloride (EDC). Initially, these researchers were unable to isolate a pure culture of the bacteria (Stucki, G., Brunner, W., Staub, D. and Leisinger, T. [1981] In Microbial Degradation of Xenobiotics and Recalcitrant Compounds, Leisinger, T. Look, A. M., Hutter, R. and Nuesch, J. eds Academic Press. London, pp 131-137), but they then proceeded to obtain such a culture (Stucki, G., Krebser, U. and Leisinger, T. [1983] Experentia 39: 1271-1273). This organism was not identified by name and was designated DE2. It could not grow on a solid medium such as agar plates.

A second bacterium which degrades EDC was described by Janssen et al. and was identified by them as *Xanthobacter autotrophicus* (Janssen, D. B., Scheper, A., Dijkhuizen, L. and Witholt, B. [1985] Applied and Environ. Microbiol. 49: 673-677). Thus, bacterial identifications which were carried out by Colaruotolo et al. (U.S. Pat. Nos. 4,477,570 and 4,493,895) and Janssen et al. supra, resulted in different bacterial strains. They also differ from the bacterium of the subject invention, which was identified as *Alcaligenes denitrificans* ss. denitrificans by the American Type Culture Collection (ATTC).

The organism DE2, which was isolated by Stucki et al. (Stucki et al. 1983, supra), is not available for comparative studies. It seems, however, to differ from both *A. denitrificans* and *X. autotrophicus* by its vitamin dependency and its inability to grow on solid media. The former two bacteria grow readily on different compositions of solid media and do not require any vitamins for growth.

The above patents and publications are evidence of the active research being conducted to find microbial systems to degrade a variety of compounds. Though much has been done in this area, there still are literally hundreds of compounds which cannot be degraded by known microbial means. Though the degradation of compounds to cleanse the environment is finding significant support from environmental groups, there is also a need to discover new microbial processes to degrade compounds to useful intermediates or end products. Throughout these efforts to find new microbes, it is clearly evident that there is no predictability as to whether any particular microbe might have desirable degradative capabilities. Basically, the science is still at the empirical stage.

BRIEF SUMMARY OF THE INVENTION

The subject invention concerns the discovery of a novel plasmid hosted by a novel microbe. The presence of the plasmid in the microbe enables the microbe to degrade chloro-aliphatic organic compounds. This novel plasmid encodes the gene(s) responsible for the degradation of such chloro-aliphatic organic compounds. The plasmid can be readily isolated from the microbe disclosed herein and, if desired, transformed into other microbial hosts by known recombinant DNA procedures. The plasmid also can be transferred to another microbial host by conjugation.

More specifically, the invention concerns a plasmid named pEDC which encodes the gene(s) responsible for the degradation of chloro-aliphatic organic compounds. Thus, a microbe hosting plasmid pEDC can be used to degrade chloro-aliphatic organic compounds when cultured under suitable conditions in the presence of the organic compound to be degraded. pEDC was named after its first recognized degradative function, i.e., ethylene chloride. The novel strain denoted BFG668.7, of the microbe *Alcaligenes denitrificans* ss. denitrificans, which hosts pEDC, is disclosed herein to exemplify the degradative features of pEDC.

DETAILED DISCLOSURE OF THE INVENTION

Figure 1:
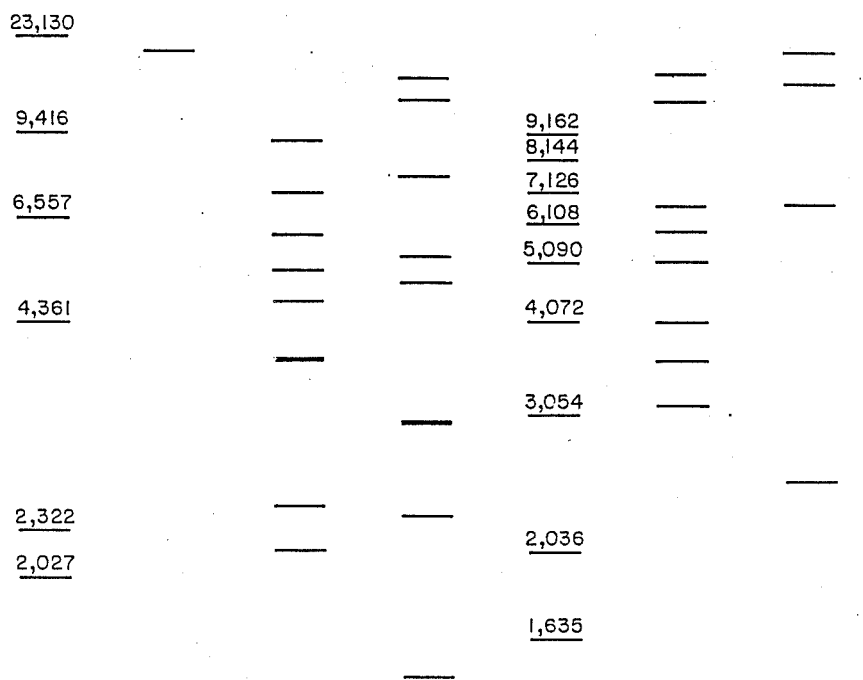
FIG. 1: Electrophoresis patterns of restriction enzyme reactions on pEDC. Lanes 1 and 5 are molecular weight standards, with Lambda DNA cut with HindIII, and one Kb ladder (Bethesda Research Labs, Gaithersburg, MD). Possible doublets were found in the PstI cut (band estimated at 3,800 bp), and in the BamHI cut (band estimated at 2,950 bp).

The novel microbe hosting plasmid pEDC of the subject invention was characterized by the American Type Culture Collection (ATCC) in Rockville, MD USA. This characterization is as follows:

| | |
|---|---|
| Isolate submitted: | BFG668.7 |
| Identified as: | *Alcaligenes denitrificans* ss. *denitrificans* |
| Morphology: | BFG is a gram negative motile rod with *peritrichous flagella*. Poly-beta-hydroxybutyrate accumulates as inclusions. |

Physiology & Biochemistry:

| | | | |
|---|---|---|---|
| Gram positive | − | Gelatinase | − |
| Gram negative | + | Tween 20 hydrolysis | − |
| Gram variable | − | Tween 80 hydrolysis | − |
| Motile at RT | + | Indole | − |
| *Flagella peritrichous* | + | Simmons citrate growth | + |
| *Flagella lophotrichous* | − | Urease | − |
| *Flagella monotrichous* | − | Nitrate to nitrite | + |
| *Flagella lateral* | − | Nitrite reduction | − |
| 4 C growth | − | Nitrite to nitrogen gas | − |
| 25 C growth | + | Hydrogen sulfide (TSI) | − |
| 30 C growth | + | Lysine decarboxylase | − |
| 37 C growth | + | Arginine (Mollers) | − |
| 41 C growth | w | Ornithine decarboxylase | − |
| Fluorescein produced | − | Phenylalanine deamination | − |
| Pyocyanine produced | − | Lecithinase | − |
| Diffusible orange | − | Phosphatase | − |
| Diffusible yellow | − | Catalase | + |
| Diffusible purple | − | Oxidase | + |
| Non-diffusible green | − | Gluconate oxidation | w |
| Other non-diff. pigments | − | Growth on malonate as SCS | + |
| Melanin pigment produced | − | Tyrosine degradation | + |
| pH 6.0 growth | + | dl-hydroxybutyrate growth | + |
| 3% NaCl growth | + | PHB accumulation | + |
| 6.5% NaCl growth | − | Deoxyribonuclease | − |
| MacConkey agar growth | + | Growth on 0.05% cetrimide | + |
| Skim milk agar growth | + | Growth on acetate as SCS | + |
| Aesculin hydrolysis | − | Testosterone deg. | − |
| Casein hydrolysis | − | | |
| Starch hydrolysis | − | | |

Sole Carbon Sources in Stanier's Mineral Base:

| | | | |
|---|---|---|---|
| L-arabinose | − | L-malate | + |
| cellobiose | − | pelargonate | − |
| D-fructose | − | propionate | + |
| D-glucose | − | quinate | − |
| lactose | − | succinate | + |
| maltose | − | L-+-tartrate | + |
| D-mannitol | − | valerate | + |
| L-rhamnose | − | B-alanine | + |
| D-ribose | − | D-A-alanine | + |
| D-sorbitol | − | betaine | − |
| sucrose | − | glycine | + |
| trehalose | − | L-histidine | + |
| D-xylose | − | DL-norleucine | + |
| adonitol | − | L-proline | + |
| erythritol | − | D-tryptophan | − |
| glycerol | W | L-valine | + |
| ethanol | − | DL-arginine | − |
| geraniol | − | benzylamine | − |
| i-inositol | − | butylamine | − |
| sebacic acid | + | putrescine | − |
| acetamide | + | mesoconate | + |
| adipate | + | DL-glycerate | + |
| benzoate | + | L-tryptophan | + |
| butyrate | + | | |
| citraconate | + | | |
| D-gluconate | + | | |
| M-hydroxybenzoate | + | | |
| 2-ketogluconate | − | | |
| DL-lactate | + | | |

Fermentation of Carbohydrates in Hugh & Leifson's O-M Medium:

| | | | |
|---|---|---|---|
| Acid from L-arabinose | K | Acid from maltose | K |
| Acid from cellobiose | K | Acid from D-mannitol | K |
| Acid from ethanol | + | Acid from D-mannose | K |
| Acid from D-fructose | K | Acid from L-rhamnose | K |
| Acid from D-glucose AO2 | K | Acid from D-ribose | K |
| Acid from D-glucose AnO2 | − | Acid from sucrose | K |
| Alkaline pH in D-glucose | − | Acid from trehalose | K |
| Acid from glycerol | K | Acid from D-xylose | K |
| Acid from i-inositol | K | | |
| Acid from lactose | K | control | K |

K = alkaline
+ = acid
− = no change
W = weak positive reaction

Comparison of Alcaligenes sp. with isolate

| | BFG668.7 | *A. denitrificans* subsp. *denitrificans* | *A. denitrificans* subsp. *xylosoxidans* | *A. faecalis* |
|---|---|---|---|---|
| Oxidase | + | + | + | + |
| Catalase | + | + | + | + |
| Peritrichous | + | + | + | + |
| Aerobic Metabolism | + | + | + | + |
| Gelatin hydrolysis | − | − | − | − |
| Acid from O-F glucose | − | − | + | − |
| Acid from O-F xylose | − | − | + | − |
| Nitrate reduced to nitrite | + | d | + | − |
| Nitrate reduction | − | d | + | + |
| Carbon Source Utilization | | | | |
| Adipate | + | + | + | − |
| Sebacate | + | + | + | − |
| Mesoconate | + | + | + | − |
| L-histidine | + | + | + | − |
| B-alanine | + | d | d | − |
| m-Hydroxybenzoate | + | + | + | − |

D = 11–89% positive

Comments on Taxonomy of Genus: The classification of the species in the genus Alcaligenes in the past was based primarily on biochemical and physiological properties, many of which were negative. Recently, studies have included carbon source utilization, DNA base composition, r-RNA-DNA homology, and gel electrophoretic protein patterns in addition to conventional phenotypic characteristics. This has brought about the clustering of strains into different groups resulting in confusing name changes.

Bergey's Manual of Systematic Bacteriology, 1984, and the Approved Lists of Bacterial Names recognize the following species:
  Alcaligenes faecalis
  *A. denitrificans* subsp. denitrificans
  *A. denitrificans* subsp. xylosoxidans Lenette, in the *Manual of Clinical Microbiology*, 1980, and Tilton in *The Procaryotes*, 1981, retain the older classification and recognize the following species:
  *A. faecalis*
  *A. odorans*
  *A. denitrificans*
  *Achromobacter xylosoxidans*

As the name implies, in the past, "*Alcaligenes denitrificans*" was retained for those strains that were able to denitrify. Studies of nitrate and nitrite reduction have shown that the test results vary greatly, depending upon medium, temperature, concentration of $NO_3$ and $NO_2$, and length of incubation. Strains now included in this species based on other criteria, may include those that are not able to denitrify. 20% of the strains now classified as *Alcaligenes denitrificans* subsp. denitrificans are not able to denitrify.

This isolate belongs to this group, and its identification is based on Bergey's, 1984, and the Approved Lists of Bacterial Names.

Bibliography

Bergey's Manual of Systematic Bacteriology, Williams & Wilkins, 1984.

Tilton, R. C. *The Genus Alcaligenes* in *The Procaryotes*, Springer-Verlag, 1981.

Pickett, M. and J. R. Greenwood. A Study of the Va-1 Group of Pseudomonas and its Relationship to *Pseudomonas pickettei*.

Skerman, V. B. D., V. McGowan, P. Smeath. Approved Lists of Bacterial Names. I.J.S.B. 30, 225–420, 1980.

Moore, W., E. Cato, L. V. Moore, Index of the Bacterial and Yeast Nomenclatural Changes Published in the *International Journal of Systematic Bacteriology* Since the 1980 Approved Lists of Bacterial Names (1 Jan. 1980 to 1 Jan. 1985) I.J.S.B. 35, 382–407, 1985.

Lennette, E. Manual of Clinical Microbiology, Glucose-Nonfermenting Gram-Negative Bacteria. 263–287, 1980.

Clark, W. A. et al. Identification of Unusualy Pathogenic Gram-Negative Aerobic and Facultatively Anaerobic Bacteria, CDC, 1984.

Kiredjian, M., M. Popoff, C. Coynault, M. Lefevre, M. Lemelin. Taxonomic due Genre Alcaligenes. Ann. Microbiol. (Inst. Pasteur) 132B, 337–374, 1981.

Yamastoto, K., M. Akagawa, N. Oishi, H. Kuraishi. Carbon Subestrate Assimilation Profiles and other Taxonomic Features of *Alcaligenes faecalis*, *Alcaligenes ruhlandii* and *Achromobacter xylosoxidans*. J. Gen. Microbiol. 28, 195–213, 1982.

Ruger, H.-J. and T. L. Tan. Separation of *Alcaligenes denitrificans* sp. nov., nom. rev. from *Alcaligenes faecalis* on the basis of DNA Base Composition, DNA homology, and Nitrate Reduction. I.J.S.B. 33, 85–89, 1983.

Pichinoty, F., M. Veron, M. Mandel, M. Durand, C. Job, J.-L. Garcia. Etude physiologique et taxonomique du genre Alcaligenes: *A. denitrificans, A. odorans*, et *A. faecalis*. Can. J. Microbiol. 24, 743–753, 1978.

A subculture of *Alcaligenes denitrificans* ss. denitrificans BFG668.7 was deposited on Mar. 12, 1986, in the permanent collection of the Agricultural Research Service Patent Culture Collection, Northern Regional Research Center, Peoria, Ill. 61604 USA to be maintained for at least 30 years. The culture was assigned the accession number NRRL B-18057 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

The novel microbe of the subject invention, BFG668.7, was discovered in the soil of a site contaminated by various chemicals, including 1,2-dichloroethane (EDC).

BFG668.7 was tested for its ability to degrade various chemical compounds. The bacteria were grown in Bushnell-Haas Broth (BHB) (Difco, Detroit, MI) on a shaker under aerobic conditions at room temperature. Growth with volatile compounds was carried out in 160 ml serum bottles capped with Teflon-lined septa (Microsep, Boulder, CO) and crimped with aluminum seals. Bottles contained 50 or 100 ml medium.

The test results are as follows:

| Compounds Tested | Degradation of Compounds |
| --- | --- |
| Chloro aromatics: | |
| 2,3-dichlorotoluene | − |
| 3,4-dichlorotoluene | − |
| o-chlorotoluene | − |
| m-chlorotoluene | − |
| p-chlorotoluene | − |
| monochlorobenzene | − |
| m-dichlorobenzene | − |
| 1,2,4-trichlorobenzene | − |
| o-chlorophenol | − |
| p-chlorophenol | − |
| Chloro-aliphatics: | |
| ethylene dichloride (EDC) | + |
| 1,1,2-trichloroethane | + |
| 1,1,1-trichloroethane | + |
| 1,2-dichloropropane | + |
| methylene chloride | + |
| trans 1,2-dichloroethylene | − |
| Chlorinated acids: | |
| chloroacetic acid | + |
| trichloroacetic acid | + |
| Other compounds: | |
| 2-chloroethanol | + |
| ethylene glycol | + |
| ethylene dibromide (EDB) | + |
| acetic acid | + |
| Control: | |
| 0.001% yeast extract | − |

Note: Positives were determined by increased turbidity at 540 nm or by production of free chloride.

Toxicity of EDC

A culture of BFG668.7 was grown with different concentrations of EDC, ranging from 2.5 to 32.5 mM. Growth, as determined by turbidity, was observed up to 17.5 mM EDC. Due to a decrease in the pH during EDC degradation, the degradation was not completed in bottles which contained more than 10 mM.

The plasmid pEDC isolated from BFG668.7, as disclosed infra, was subjected to restriction enzyme analysis.

pEDC was restricted with several restriction enzymes. The restriction enzymes which were used require six base pairs of DNA for a recognition of a restriction site. Yet no unique cuts (which result in a single cut of the plasmid) were found using PstI, BamHI, XhoI, or EcoRI enzymes. FIG. 1 shows the cut patterns of these enzymes, the "foot prints" of the plasmid. Together with the restriction enzyme reactions, the intact plasmid (in covalently closed circular form), and two molecular weight standards were used. The first was Lambda DNA cut with the enzyme HindIII (BRL), and the second was one Kb ladder. The numbers above the bands on these standards are the molecular size of the bands in base pairs.

Between 4–9 bands were recognized for each enzyme. Total plasmid size, as estimated from these cuts, ranged between 40.82–54.57 Kb, as follows: PstI, 45,150 bp; BamHI, 47,530 bp; EcoRI, 54,570 bp; and XhoI, 40,820 bp.

Following is the summary of the estimated sizes of the restriction enzyme reaction products.

| PstI cut | | BamHI cut | | EcoRI cut | | XhoI cut | |
|---|---|---|---|---|---|---|---|
| (a) | bp | (a) | bp | (a) | bp | (a) | bp |
| 616 | 9,100 | 558 | 12,500 | 548 | 14,600 | 530 | 19,800 |
| 661 | 7,400 | 574 | 11,200 | 572 | 11,500 | 565 | 11,900 |
| 707 | 6,050 | 678 | 6,800 | 690 | 6,400 | 685 | 6,600 |
| 738 | 5,400 | 738 | 5,400 | 713 | 5,900 | 970 | 2,520 |
| 772 | 4,850 | 766 | 4,900 | 750 | 5,200 | | |
| 840 | 3,800 (b) | 912 | 2,950 (b) | 809 | 4,220 | | |
| 960 | 2,600 | 1004 | 2,300 | 851 | 3,650 | | |
| 1034 | 2,150 | 1178 | 1,480 | 901 | 3,100 | | |

(a) Arbitrary units. The distance was measured using a slide projector in order to decrease measurement error. The relative distances of the restriction enzyme cut products and the standards are fix. Lambda DNA, cut with HindIII, and 1 Kb ladder (BRL), were used as molecular weight standards.
(b) Possible doublet.

pEDC was shown to encode the gene(s) responsible for the degradation of chloro-aliphatic organic compounds.

The subject invention, i.e., plasmid pEDC when present in BFG668.7 or in another host microbe, can be used for the degradation of obnoxious organic wastes into innocuous materials. These entities are particularly useful to degrade chloro-aliphatic organics, as described herein. The degradation process can be carried out by adding liquid culture media of a microbe hosting pEDC, e.g., BFG668.7, to chloro-aliphatic wastes in the soil or water. In general, the process of degradation can be carried out as disclosed in U.S. Pat. No. 4,477,570, columns 13, 14 and 15. Further, the subject invention can be used generally according to procedures disclosed in U.S. Pat. No. 4,483,923. Thus, it should be recognized that wherever the invention entities are used, the conditions must be such that growth of the microbe is possible, since the microbe must be viable in order to utilize, and thus degrade, target organics. Factors such as temperature and pH must be ascertained and monitored in order to achieve the maximum effectiveness from the subject invention entities. Generally, the microbe hosting pEDC, e.g., BFG668.7, can be cultured at about 15° C. to about 42° C., preferably about 20° C. to about 38° C. Advantageously, the pH should be in the range of about 5.5 to about 8.5, preferably about 6.5 to about 8.0. The pH can be controlled by procedures well known in the art.

It should be recognized that growth conditions may vary with different microbes hosting plasmid pEDC. Basically, the known growth conditions for each microbe hosting pEDC will be used. Where necessary, adjustments can be readily made by a person of ordinary skill in the art without undue experimentation.

EDC concentrations

EDC concentrations were determined by gas liquid chromatograph using Porasil C (100–200 mesh) column (Waters, Milford, MA) with Carbowax 400. EDC was eluted at about 8.5 min at 50° C. Samples were removed from culture bottles by syringe, placed into 2.0 ml glass vials and sealed with Teflon-lined seals. Five $\mu$l of the samples were directly injected. The results were compared with a standard curve of EDC. The standard curve was prepared by introduction of different amounts of EDC into 50 ml of sterile BHB in serum bottles sealed with Teflon-lined caps. The bottles were incubated at room temperature on a shaker for 12–24 hr.

Chloride ion concentrations

Chloride ion concentrations were measured either by specific ion electrode (Orion model 96-17B combination electrode with microprocessor Ionalyzer model 901 (available from Orion Research Co., Cambridge, MA) or by anion exchange HPLC on an IC-PAK anion column (Waters). Samples for HPLC were prefiltered through a 0.2 $\mu$m GA-8 filter (Gelman Sciences, Ann Arbor, MI).

pH and turbidity pH was measured using Orion model 91-02 electrode with the microprocessor Ionalyzer model 901.

Turbidity was measured as the absorbance at 540 nm on a Spectronic 20 spectrophotometer (Bausch and Lomb, Rochester, NY).

Gel electrophoresis conditions

Standard conditions consisted of horizontal minigel (Model H6 Baby Gel, BRL, Gaithersburg, MD) 0.7% agarose (BRL) in Tris-borate-ethylenediaminetetraacetic acid (TBE) (11.3 g/l Tris base [BRL], 5.5 g/l boric acid [Aldrich, Milwaukee, WI], and 0.92 g/l sodium ethylenediaminetetraacetic acid [EDTA] [Aldrich]), and ethydium bromide (1 $\mu$l of 10 mg/ml per 20 ml gel). TBE also served as a running buffer. The samples were run at 75 V constant for 75 min.

Restriction enzymes were obtained from BRL and were used according to the manuufacturer's recommended conditions.

Following are examples which illustrate procedures, including the best mode, for practicing the invention. These examples should not be construed as limiting. All percentages are by weight and all solvent mixture proportions are by volume unless otherwise noted.

EXAMPLE 1—ISOLATION OF BFG668.7 FROM A SOIL SAMPLE

Soil samples from a site contaminated with halogenated organics, including EDC, were enriched for EDC degradation by repetitive transfers on minimal medium with EDC as a major carbon and energy source. Minimal medium contained 3.0 g/l $K_2HPO_4$, 3.0 g/l $KH_2PO_4$, 1.5 g/l $(NH_4)_2SO_4$, 0.2 g/l $MgSO_4.H_2O$, and 100 ml/l of hot water soil extract. Hot water soil extract was prepared by 30 min autoclaving of 200 g fertile (garden) soil with 150 ml distilled water, and filtration through #1 Whatman filter. EDC concentrations ranged between 1.0 and 10.16 mM. Samples were grown at room temperature under aerobic conditions on a reciprocal shaker for 7 days. This enrichment resulted in the complete degradation of EDC and the production of 2 moles chloride for each mole of EDC degraded by a mixed bacterial population.

The enriched mixed population was subjected to fast transfers and plating on selective medium (Bushnell-Haas Agar, Difco) with EDC as a sole carbon souce. Isolated colonies were transferred back to liquid medium. Four biologically pure cultures were obtained which were able to demonstrate utilization of EDC as a sole carbon and energy source. One culture, a gram negative rod, designated BFG668.7, was subjected to further investigation.

EXAMPLE 2—ISOLATION OF pEDC FROM BFG668.7

BFG668.7 was grown in 1,500 μl of ethylene glycol or chloroethanol for 1–2 days. The grown culture was centrifuged at 15,000 g for 20 min. Pellets were resuspended in 20 ml TE (10 mM Tris HCl pH 8.4, and 1 mM EDTA), transferred to 15 ml centrifuge tubes and spun down at 3,200 g for 5 min. From this point, the procedure is given for each tube. Supernatant was discarded and the pellet was resuspended in 1 ml TE, vortexed on ice, and transferred to a 1.5 ml tube. The suspension was spun down in a microfuge for 1 min. The supernatant was poured out carefully, and the pellet was resuspended by vortexing in 0.5 ml of 0.15% sucrose, 50 mM Tris HCl, and 25 mM EDTA at pH 8.0. The centrifuge tube was cooled on ice for 5–10 min. 100 μl of 2% freshly made lysozome solution was added and the tube was mixed gently by inversions. After 10 min incubation on ice, 200 μl of 0.2% Triton X, 100 mM Tris HCl, and 100 mM EDTA at pH 8.5 were added and incubated on ice for 10 min. The tubes were spun for 10 min at 4° C. The supernatant was poured to new tubes, the pellet discarded, and 6 μl diethylpyrocarbonate (DEPC) were added. With the cap open, the tube was incubated for 15 min at 65° C., followed by cooling on ice for 3 min. After addition of 250 units of RNase Tl, the tube was incubated at 37° C. for 20 min, and spun for 2 min. The supernatant was transferred to a new tube and the pellet was discarded. The plasmid preparation was then subjected to ethanol precipitation and phenol extraction (Maniatis, T., Fritsch, E. F. and Sambrook, J. [1982] *Molecular Cloning, A Laboratory Manual*, Cold Spring Harbor Laboratory, Cold Spring Harbor, NY) to give essentially pure pEDC.

EXAMPLE 3—TRANSFORMATION

Plasmid preparations of pEDC, prepared as described in Example 2, were used for transformation. Recipient organisms included *A. denitrificans* which lost its ability to grow on EDC or ethylene glycol as a sole carbon and energy source, and known and available *E. coli* strain ATCC 27662-1. Prior to the transformation experiment, both organisms expressed their ability to grow on a single carbon source in minimal medium (acetate and glucose, respectively). Transformation experiments were done using the method described by Maniatis et al. (1982, Molecular Cloning, A Laboratory Manual).

Each of these organisms were incubated together with a pEDC preparation that did not contain any live cells.

Since both of the recipient organisms grew on a rich medium, Tryptic Soy Broth (TSB, Difco), they were checked for their ability to grow on minimal medium with a single carbon source. Both were shown to grow on a single carbon source in a salt medium (BHB). *A. denitrificans* grew on acetate, and *E. coli* grew on glucose without the addition of vitamins or amino acids. The test compound for the transformation was ethylene glycol. It was shown that when A. denitrificans lost its ability to metabolize EDC, it also lost the ability to grow on ethylene glycol. Ethylene glycol, when added to rich medium (TSB) did not inhibit the growth of the recipient bacteria. After the transformation, both of the transformed bacteria showed good growth on ethylene glycol as a sole carbon and energy source. Large numbers of organisms are involved in the initial transformation steps. Thus, no turbidity measurements can be taken during that stage. Turbidity was taken after the cultures were transferred and regrown on ethylene glycol. The results are as follows:

|  | Turbidity at 540 nm | |
|---|---|---|
|  | t = 0 | t = 25d |
| Transformed Cultures |  |  |
| *E. coli* | 0.07 | 0.25 |
| *A. denitrificans* | 0.13 | 0.21 |
| Control cultures |  |  |
| *E. coli* | 0.07 | 0.08 |
| *A. denitrificans* | 0.07 | 0.03 |

The cultures were subjected to plasmid isolation procedure and were run on electrophoresis agarose gel. Only the transformed cultures showed clear bands which correspond in their migration to pEDC.

Microbes transformed with plasmid pEDC by conjugation or recombinant DNA means can be used in a mixture with other microbes so long as the mixture does not inhibit the degradative properties of the microbe hosting plasmid pEDC, e.g., BFG668.7. Such a mixture can be used, advantageously, to broaden the scope of chemical compounds degradable in, for example, a contaminated land site. For example, plasmid pEDC in a microbial host, e.g., BFG668.7, can be used with the microbes disclosed by the patents listed in the Background of the Invention. It is clear to a person skilled in this art that the microbial preparations used need not be biologically pure so long as the impurity does not inhibit the degradative properties of the microbe hosting plasmid pEDC.

Plasmid pEDC can be used to transform prokaryotic and eukaryotic microbial hosts by standard procedures. See Maniatis, T., Fritsch, E. F. and Sambrook, J. (1982) *Molecular Cloning: A Laboratory Manual*, Cold Spring Harbor Laboratory, New York. The DNA in plasmid pEDC encoding the degradative activities as disclosed herein can be probed and isolated from plasmid pEDC by known procedures and used to prepare other vectors which can then be used to transform other microbial hosts. For example, pEDC DNA encoding the degradative activities can be expressed in *Saccharomyces cerevisiae* using plasmids containing the inducible galactose promoter from this organism (Broach, J. R., Li, Y., Wu, L. C. and Jayaram, M. in Experimental Manipulation of Gene Expression [1983] p. 83, ed. M. Inouye, Academic Press). These plasmids are called YEp51 and YEp52 (Broach, J. R. et al. [1983]) and contain the *E. coli* origin of replication, the gene for β-lactamase, the yeast LEU2 gene, the 2 μm origin of replication and the 2 μm circle REP3 locus. Recombinant gene expression is driven by the yeast GAL10 gene promoter.

Yeast promoters such as galactose and alcohol dehydrogenase (Bennetzen, J. L. and Hall, B. D. [1982] J. Biol. Chem. 257: 3018; Ammerer, G. in Methods in Enzymology [1983] Vol. 101, p. 192), phosphoglycerate kinase (Derynck, R., Hitzeman, R. A., Gray, P. W., Goeddel, D. V., in Experimental Manipulation of Gene Expression [1983] p. 247, ed. M. Inouye, Academic Press), triose phosphate isomerase (Alber, T. and Kawasaki, G. [1982] J. Molec. and Applied Genet. 1: 419), or enolase (Innes, M. A. et al. [1985] Science 226: 21) can be used.

As disclosed above, it is well within the skill of those in the genetic engineering art to use the DNA obtainable from plasmid pEDC to make other vectors. Fusing the DNA into an expression vector and transforming or transfecting into hosts, either eukaryotic (yeast or mammalian cells) or prokaryotic (bacterial cells), are standard procedures in the art.

In summary, various methods employed in the preparation of plasmids and transformation of host organisms are well known in the art. These procedures are all described in Maniatis, T. et al. supra. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

I claim:

1. A process for degrading chloroaliphatic organic compounds which comprises growing a microbe hosting plasmid pEDC, alone or in mixture with other microbes, in the presence of the organic compounds to be degraded.

2. A process, according to claim 1, wherein said organic compounds are selected from the group consisting of chloro-aliphatics, chlorinated acids, 2-chloroethanol, ethylene glycol, ethylene dibromide, and acetic acid.

3. A process, according to claim 2, wherein said chloro-aliphatics are selected from the group consisting of ethylene dichloride, 1,12-trichloroethane, 1,1,1-trichloroethane, 1,2-dichloropropane and methylene chloride.

4. A process, according to claim 2, wherein said chlorinated acids are chloroacetic acid or trichloroacetic acid.

5. A process, according to claim 1, wherein said microbe hosting plasmid pEDC is *Alcaligenes denitrificans* ss. denitrificans, having the identifying characteristics of BFG668.7.

6. A process for degrading ethylene dichloride which comprises growing a microbe hosting plasmid pEDC, alone or in mixture with other microbes, in the presence of ethylene dichloride.

7. A process, according to claim 6, wherein said microbe hosting plasmid pEDC is *Alcaligenes denitrificans* ss. denitrificans, having the identifying characteristics of BFG668.7.

* * * * *

UNITED STATES PATENT AND TRADEMARK OFFICE
CERTIFICATE OF CORRECTION

PATENT NO. : 4,806,482
DATED : February 21, 1989
INVENTOR(S) : Amikam Horowitz

It is certified that error appears in the above-identified patent and that said Letters Patent is hereby corrected as shown below:

Column 9:     line 4: After "1,500" insert -- ml of minimal medium, as described in Example 1, with 1,500 --.

Column 12:    line 5: "1,12-trichloroethane" should read --1,1,2-trichloroethane--.

Signed and Sealed this

Nineteenth Day of December, 1989

*Attest:*

JEFFREY M. SAMUELS

*Attesting Officer*     *Acting Commissioner of Patents and Trademarks*